United States Patent
Yamamoto et al.

(10) Patent No.: US 6,894,202 B1
(45) Date of Patent: May 17, 2005

(54) METHOD FOR PRODUCING 2,6-DIMETHYLNAPHTHALENE

(75) Inventors: Koji Yamamoto, Kobe (JP); Seiichi Yamamoto, Kobe (JP); Takeharu Tanaka, Kobe (JP); Masahiro Motoyuki, Osaka (JP); Shingo Yoshida, Osaka (JP)

(73) Assignee: Kobe Steel, Ltd., Kobe (JP)

( * ) Notice: Subject to any disclaimer, the term of this patent is extended or adjusted under 35 U.S.C. 154(b) by 48 days.

(21) Appl. No.: 10/069,502

(22) PCT Filed: Aug. 30, 2000

(86) PCT No.: PCT/JP00/05844

§ 371 (c)(1),
(2), (4) Date: Feb. 27, 2002

(87) PCT Pub. No.: WO01/16061

PCT Pub. Date: Aug. 3, 2001

(30) Foreign Application Priority Data

Aug. 31, 1999 (JP) .......................................... 11/246299

(51) Int. Cl.$^7$ ................................................ C07C 7/14
(52) U.S. Cl. ........................ 585/814; 585/812; 585/815; 585/816; 585/817
(58) Field of Search ............................... 585/812, 814, 585/815, 816, 817

(56) References Cited

U.S. PATENT DOCUMENTS

| | | | |
|---|---|---|---|
| 5,723,711 A | 3/1998 | Motoyuki et al. |
| 5,744,670 A | 4/1998 | Motoyuki et al. |
| 6,011,190 A | 1/2000 | Motoyuki et al. |
| 6,018,086 A | 1/2000 | Motoyuki et al. |
| 6,018,087 A | 1/2000 | Motoyuki et al. |
| 6,121,501 A | 9/2000 | Motoyuki et al. |
| 6,153,808 A | 11/2000 | Motoyuki et al. |

FOREIGN PATENT DOCUMENTS

| EP | 0 939 068 | 9/1999 |
|---|---|---|
| JP | 48-5767 | 1/1973 |
| JP | 48-22449 | 3/1973 |
| JP | 5-331079 | 12/1993 |
| JP | 9-176054 | 7/1997 |
| JP | 9-278682 | 10/1997 |

OTHER PUBLICATIONS

U.S. patent application Ser. No. 09/965,822, filed Oct. 1, 2002, pending.

U.S. patent application Ser. No. 10/069,502, filed Feb. 27, 2002, pending.

U.S. patent application Ser. No. 10/069,502, Yamamoto et al., filed Feb. 27, 2002.

U.S. patent application Ser. No. 10/193,228, Motoyuki et al., filed Jul. 12, 2002.

*Primary Examiner*—Walter D. Griffin
*Assistant Examiner*—Tam Nguyen
(74) *Attorney, Agent, or Firm*—Oblon, Spivak, McClelland, Maier & Neustadt, P.C.

(57) ABSTRACT

An object of the present invention is to provide a method for manufacturing 2,6-DMN, in which even when a mixture containing DMN isomers which includes 5 wt % or more of 2,7-DMN is used, a highly pure 2,6-DMN can be obtained. The method for manufacturing the highly pure 2,6-dimethylnaphthalene of the present invention comprises performing cooling crystallization of a mixture containing dimethylnaphthalenes which includes 2,6-dimethylnaphthalene, performing solid-liquid separation to obtain a solid component, and washing the solid component using a solvent, wherein the solid-liquid separation performed after the cooling crystallization includes press filtration. In the present invention, the pressure of the press filtration is preferably 10 kg/cm$^2$ or more, and according to the method of the present invention, even when a DMN mixture containing 5 wt % or more of 2,7-DMN is used as a feedstock, a highly pure 2,6-DMN can be manufactured, and in addition, even when a DMN mixture containing less than 25 wt % of 2,6-DMN is processed by cooling crystallization, a highly pure 2,6-DMN can be manufactured.

13 Claims, 3 Drawing Sheets

METHOD FOR PRODUCING 2,6-DIMETHYLNAPHTHALENE

This application is a 371 of PCT/JP00/05844 filed Aug. 30, 2000.

TECHNICAL FIELD

The present invention relates to a method for manufacturing 2,6-dimetylnaphthalene which can be used effectively as, for example, a feedstock for 2,6-naphthalene dicarboxylic acid which is used for forming polyesters or the like.

BACKGROUND ART

In order to obtain the superior features of polyethylene naphthalate which is used for manufacturing fibers, films, and the like, which are primarily formed of polyethylene naphthalate, it is necessary that 2,6-naphthalene dicarboxylic acid, which is a monomer component for forming a polymeric material, have a high purity, and accordingly, it is also desirable that 2,6-dimethylnaphtahlene (hereinafter, dimethylnaphthalene will be referred to as DMN regardless of the positions of substituent methyl groups) for forming the monomer component have a high purity. DMN has 10 isomers, and a highly pure 2,6-dimethylnaphthalene (preferably having a purity of 99% or more), which is mixed with substantially none of the other 9 isomers, is preferably used.

As a method for manufacturing the 2,6-DMN described above, there may be mentioned a method of separating 2,6-DMN from an isomer mixture obtained by isomerizing 1,5-DMN which is formed by a reaction between orthoxylene and butadiene; a method comprising methylating naphthalene or methylnaphthalenes, subsequently isomerizing, and separating 2,6-DMN; and a method of separating 2,6-DMN from a tar or an oil fraction. However, the fractions and the products described above are each a mixture containing many types of DMN isomers in addition to 2,6-DMN, and hence, the 2,6-DMN must be separated from the mixture described above. However, since the boiling points of these DMN isomers are very close to each other, it has been difficult to separate a highly pure 2,6-DMN therefrom by distillation which is commonly used for separation/purification of organic compounds.

Accordingly, as a method for separating this 2,6-DMN, a crystallization method or an adsorption method has been proposed, and in addition to these methods mentioned above, for example, a method comprising forming a complex by using a certain organic compound, separating the complex, and decomposing this separated complex, and combinations of the methods described above have also been proposed. A cooling crystallization method is a method exploiting the property of 2,6-DMN having a highest melting point among the 10 types of DMN isomers, and since the cooling crystallization method is simple compared to the methods described above, this method can be used suitably as an industrial separation method. However, since it has been difficult to obtain a 2,6-DMN having a purity of 99% or more only by the cooling crystallization method, a process such as treatment using a solvent is generally used together therewith. For example, in Japanese Unexamined Patent Application Publication Nos. 48-5767 and 48-22449, and Japanese Examined Patent Application Publication No. 50-22553, a method has been disclosed in which after a mixture containing DMN isomers is crystallized by cooling, solid-liquid separation is performed by suction filtration, and the obtained solid component is dissolved in a solvent and is then crystallized by cooling. However, according to the related arts described above, a DMN mixture which primarily includes specific DMN isomers among the 10 types of isomers, such as 2,6-DMN, 1,6-DMN, and 1,5-DMN, which are easily isomerized to each other and are easily separated, is used as a feedstock, and a specific DMN mixture in which the content of 2,7-DMN which is difficult to separate from 2,6-DMN is limited to less than 5 mole percent (approximately equivalent to 5 wt) is used. A mixture containing DMN isomers obtained in a typical manufacturing process generally includes 5 wt % or more of 2,7-DMN, and hence, when a mixture containing DMN isomers which includes 5 wt % or more of 2,7-DMN is used as a feedstock in accordance with the related art disclosed in the publications described above, it has been difficult to obtain a highly pure 2,6-DMN.

In view of the situations described above, the present invention was made, and an object of the present invention is to provide a method for manufacturing a highly pure 2,6-DMN even when a mixture containing DMN isomers which includes 5 wt % or more of 2,7-DMN is used as a feedstock.

DISCLOSURE OF INVENTION

A method for manufacturing 2,6-dimethylnaphthalene according to the present invention, which can solve the problems described above, comprises a step of performing cooling crystallization of a mixture containing dimethylnaphthalenes which includes 2,6-dimethylnaphthalene; a step of performing solid-liquid separation to obtain a solid component; and a washing step of washing the solid component using a solvent; wherein the solid-liquid separation performed after the cooling crystallization includes press filtration.

In addition, in a method for manufacturing a highly pure 2,6-dimethylnaphthalene according to the present invention comprising a step of performing cooling crystallization of a mixture containing dimethylnaphthalenes which includes 2,6-dimethylnaphthalene, a step of performing solid-liquid separation to obtain a solid component, and a washing step of washing the solid component using a solvent, the washing step may be performed at least twice, and a part or the entirety of a mother liquor obtained in a second washing step or in a subsequent washing step may be used as a solvent in a washing step performed prior to the washing step at which the mother liquor is obtained.

In the method described above, the mixture containing dimethylnaphthalenes may be a mixture composed of dimethylnaphthalene isomers.

In the method of the present invention, the pressure of the press filtration is preferably 10 kg/cm$^2$ or more, and the press filtration is preferably performed using a tube press.

In addition, a mixture containing dimethylnaphthalenes, which includes 5 wt % or more of 2,7-dimethylnaphthalene, may be used as a feedstock, and the cooling crystallization may be performed for a mixture containing dimethylnaphthalenes which includes less than 25 wt % of 2,6-dimethylnaphthalene. In both cases described above, a highly pure 2,6-dimethylnaphthalene can be manufactured.

In particular, when the washing step is performed for a solid component containing 80% or more of 2,6-dimethylnaphthalene by using a solvent, and subsequently, solid-liquid separation and distillation are performed, a 2,6-dimethylnaphthalene having a high purity of 99% or more may be obtained.

According to the present invention, as the solvent used in the washing step, an aliphatic hydrocarbon and/or alicyclic hydrocarbon having 5 to 10 carbon atoms are preferably used.

BEST MODE FOR CARRYING OUT THE INVENTION

In the case in which 2,6-DMN is separated by cooling crystallization and filtration from a mixture containing DMN isomers, which includes 5 wt % or more of 2,7-DMN, used as a feedstock, when the mixture containing DMN isomers is crystallized by cooling, the viscosity of a slurry of the mixture containing DMN isomers is increased. When the suction filtration is performed for this slurry in order to obtain 2,6-DMN, the separation efficiency from the mother liquor is low, and hence, it is difficult to obtain a highly pure 2,6-DMN.

The inventors of the present invention carried out intensive research on the most significant subject that is to obtain a highly pure 2,6-DMN from a mixture containing DMN isomers, which includes 5 wt % or more of 2,7-DMN, used as a feedstock. As a result, it was discovered that when press filtration was incorporated in a solid-liquid separation process which was performed after cooling crystallization, a highly pure 2,6-DMN can be manufactured even when a mixture containing DMN isomers which includes 5 wt % or more of 2,7-DNM is used, whereby the present invention was made.

In the solid-liquid separation process, press filtration may be performed after a part of a mother liquor is removed by centrifugation from a slurry obtained by cooling crystallization, or may be preferably performed for a slurry obtained right after cooling crystallization.

As a press filtration method, for example, a tube press, a filter press, a plate press, a cage press, a belt press, a screw press, or a disc press method may be mentioned. Among these methods mentioned above, a method which can perform press filtration at a higher pressure is preferable when used for industrial mass production, and above all, the tube press method in which a high pressure of 100 kg/cm$^2$ or more can be applied is preferably used.

Figure 2A:
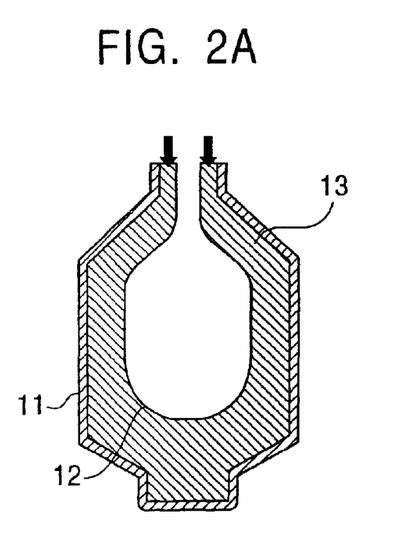
FIG. 2 includes views for illustrating a tube press method which is a typical example of press filtration.
Figure 2B:
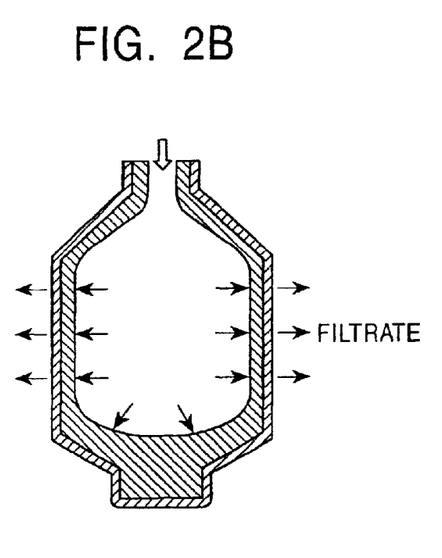

The basic principle of the tube press method is as shown in FIGS. 2(a) and (b). For example, a rubber-made cylinder 12 is concentrically provided inside a perforated cylinder 11 formed of a screen wound with a filter cloth, a slurry 13 is supplied into the annular gap formed between the two cylinders, and a high-pressure liquid is fed in the rubber-made cylinder so as to squeeze filtrate out of the perforated cylinder 11, whereby press filtration of the slurry 13 can be performed. The tube press method described above has been used in applications such as sludge treatment, but has not been used in the organic chemical industrial field since the rubber film made of raw rubber is dissolved in an organic solvent. However, as the rubber film described above, a fluorinated elastomer (polyfluorocarbon, for example, "Viton" manufactured by E. I. du Pont), which is insoluble in an organic solvent, has been developed in recent years, and hence, the tube press method can be used for the manufacturing method of the present invention.

As the mixture containing DMN isomers which is processed by cooling crystallization in the present invention, a mixture containing 5 wt % or more of 2,7-DMN may be used, and in addition, a mixture containing 10 wt % or more of 2,6-DMN is preferably used. When the content of 2,6-DMN in a feedstock less than 10 wt %, a mixture containing DMN isomers which includes 2,6-DMN at a low purity is preferably distilled so as to increase the concentration of 2,6-DMN to 10 wt % or more.

This mixture containing DMN isomers is processed by cooling crystallization to form a slurry, and the solid-liquid separation is performed for the slurry by press filtration, thereby yielding a highly pure 2,6-DMN. A crystal of the mixture containing DMN isomers, which is a solid component, is fed into a solvent for washing. A slurry containing the crystal obtained after washing is processed by solid-liquid separation using a common method such as centrifugation, and the solid thus separated is distilled for removing the solvent, thereby yielding a highly pure 2,6-DMN.

In the mixture containing DMN isomers obtained after cooling crystallization, in addition to 2,6-DMN, the other nine DMN isomers and other alkylnaphthalenes are contained, and most of the components are present in a liquid state (partly in a solid state). When these isomers are contained at high contents in the crystal obtained after solid-liquid separation, it is difficult to obtain a highly pure 2,6-DMN even after subsequent washing treatment. In order to obtain a highly pure 2,6-DMN, it is important to sufficiently perform solid-liquid separation by press filtration performed after cooling crystallization. Accordingly, the higher the pressure during press filtration, the better the separation effect is. The pressure is preferably 10 kg/cm$^2$ or more, is more preferably 50 kg/cm$^2$ or more, and is even more preferably 80 kg/cm$^2$ or more.

By these cooling crystallization and press operation described above, the purity of 2,6-DMN in the mixture containing DMN isomers is preferably increased to 80% or more. Impurities in a liquid state present in the mixture containing DMN isomers, which contains 80% or more of 2,6-DMN, can be easily removed by washing using a solvent, and a high purity of 99% or more can be finally obtained. In the case in which the purity of 2,6-DMN cannot be 80% or more when the operation of the cooling crystallization followed by the press filtration is performed once (hereinafter, operation performed once may be referred to as "single stage" in some cases), the purity of 2,6-DMN is preferably increased to 80% or more by repeating the operation of the cooling crystallization followed by the press filtration (hereinafter, operation performed at least twice may be referred to as "multistage" in some cases). Since 2,6-DMN and 2,7-DMN have similar structures and properties to each other, their behaviors are also similar to each other, and hence, it is believed that most of impurities in a solid state present in the crystal of the mixture containing DMN isomers obtained after solid-liquid separation is 2,7-DMN. However, when the purity of 2,6-DMN is increased to 80% or more, and the content of 2,7-DMN in the crystal is decreased, alkylnaphthalenes and the DMN isomers other than 2,6-DMN and 2,7-DMN, which are present in a liquid state, serve as a solvent to dissolve 2,7-DMN, and hence, most of this 2,7-DMN can be easily removed together with other impurities in a liquid state. On the other hand, when the purity of 2,6-DMN is less than 80%, the amount of a 2,7-DMN present in the crystal form is increased, and hence, it becomes difficult to remove 2,7-DMN only by washing. In addition, concerning a small amount of a 2,7-DMN in a solid state present in the crystal of the mixture containing DMN isomers obtained after solid-liquid separation, since the solubility of 2,7-DMN in a solvent is higher than that of 2,6-DMN, and 2,7-DMN is preferentially dissolved in a solvent, 2,7-DMN can be extracted from the crystal of the mixture containing DMN isomers by washing using a solvent.

The solvent used in washing treatment of the present invention is not specifically limited as long as it is in a liquid state at an operation temperature condition and is easily separated from DMN, and an aliphatic hydrocarbon or an alicyclic hydrocarbon is preferably used. The number of carbon atoms of an aliphatic hydrocarbon or an alicyclic hydrocarbon is preferably in the range of 5 to 10, and for example, hexane or octane may be mentioned.

The amount of a solvent on a weight basis is preferably at least one-third, is more preferably at least one times, is preferably at most 50 times, and is more preferably at most 5 times of the crystal of the mixture containing DMN isomers which primarily includes 2,6-DMN. In addition, the temperature range in washing treatment is preferably—10° C. or more, is more preferably 5° C. or more, is preferably 45° C. or less, and is more preferably 30° C. or less.

Figure 3:
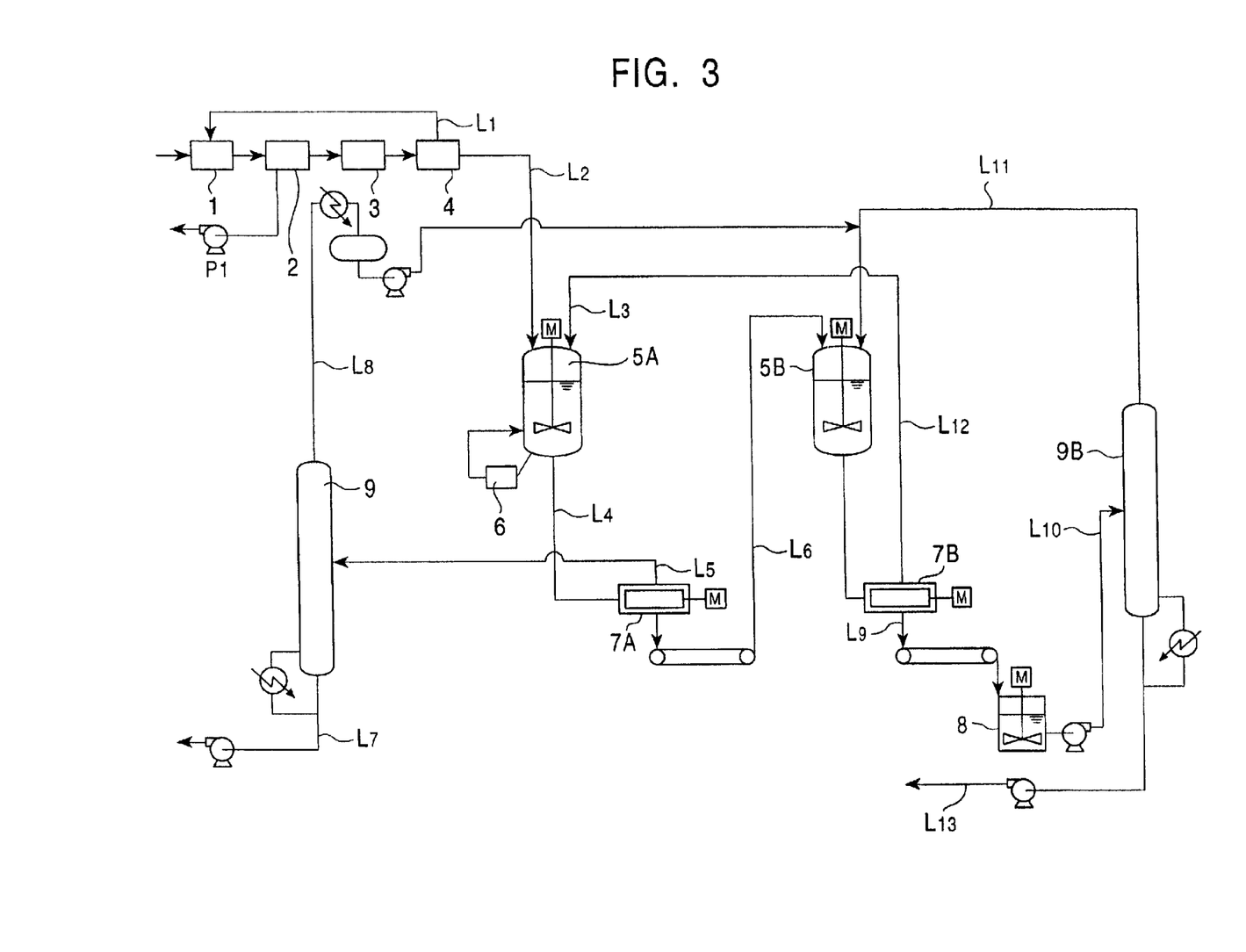
FIG. 3 is a schematic diagram showing a typical example of a method of the present invention.

As described above, by the washing treatment using a solvent, 2,7-DMN can be removed from the crystal of the mixture containing DMN isomers by extraction; however, when the content of 2,7-DMN is high, a 2,6-DMN having a high purity of 99% or more may not be obtained in some cases by performing the washing treatment once. In the case described above, a highly pure 2,6-DMN can be obtained by performing the washing treatment at least twice; however, when the washing treatment using a solvent is simply performed at least twice, the yield of 2,6-DMN may be significantly decreased in some cases. Accordingly, in order to prevent the decrease in yield described above, when the washing treatment is performed at least twice, as shown in FIG. 3 by way of example, a mother liquor obtained at a second or a subsequent washing treatment is used as a washing solvent at washing treatment prior to the washing treatment at which the mother liquor is obtained, whereby the purity of 2,6-DMN can be increased without decreasing the yield thereof.

Since a mother liquor obtained by washing treatment is a saturated solution of 2,6-DMN, 2,6-DMN is not further dissolved in the mother liquor when washing is performed using the solution described above. On the other hand, since impurities other than 2,6-DMN are not saturated, they are dissolved in this solution. Accordingly, when a mother liquor obtained by washing treatment is used as a washing solvent at washing treatment prior to the washing treatment at which the mother liquor is obtained, the purity can be increased without decreasing the yield of 2,6-DMN.

A solid component which is processed by the washing treatment described above at least twice is preferably obtained by cooling crystallization followed by the press filtration as described above; however, a solid component processed by solid-liquid separation using a method other than the press filtration may also be used.

In the present invention, since a crystal of the mixture containing DMN isomers obtained by press has a large block-shaped lump, when this crystal is dipped in a solvent for washing, it is difficult to remove impurities present at an inner side of the lump, and hence, the efficiency is low. Accordingly, the washing efficiency is preferably improved by providing a circulating pump outside a washing bath for circulating a slurry therein and by pulverizing a cake to be washed using a wet-type pulverizer.

After a solvent separated from a highly pure 2,6-DMN by distillation or a solvent obtained by solid-liquid separation is processed by distillation so as to remove a solute, they may be reused for washing treatment.

Hereinafter, the present invention will be described with reference to figures; however, the present invention is not limited to the figures described below, and it is understood that every modification made in accordance with the description in this specification is within the scope of the present invention.

Figure 1:
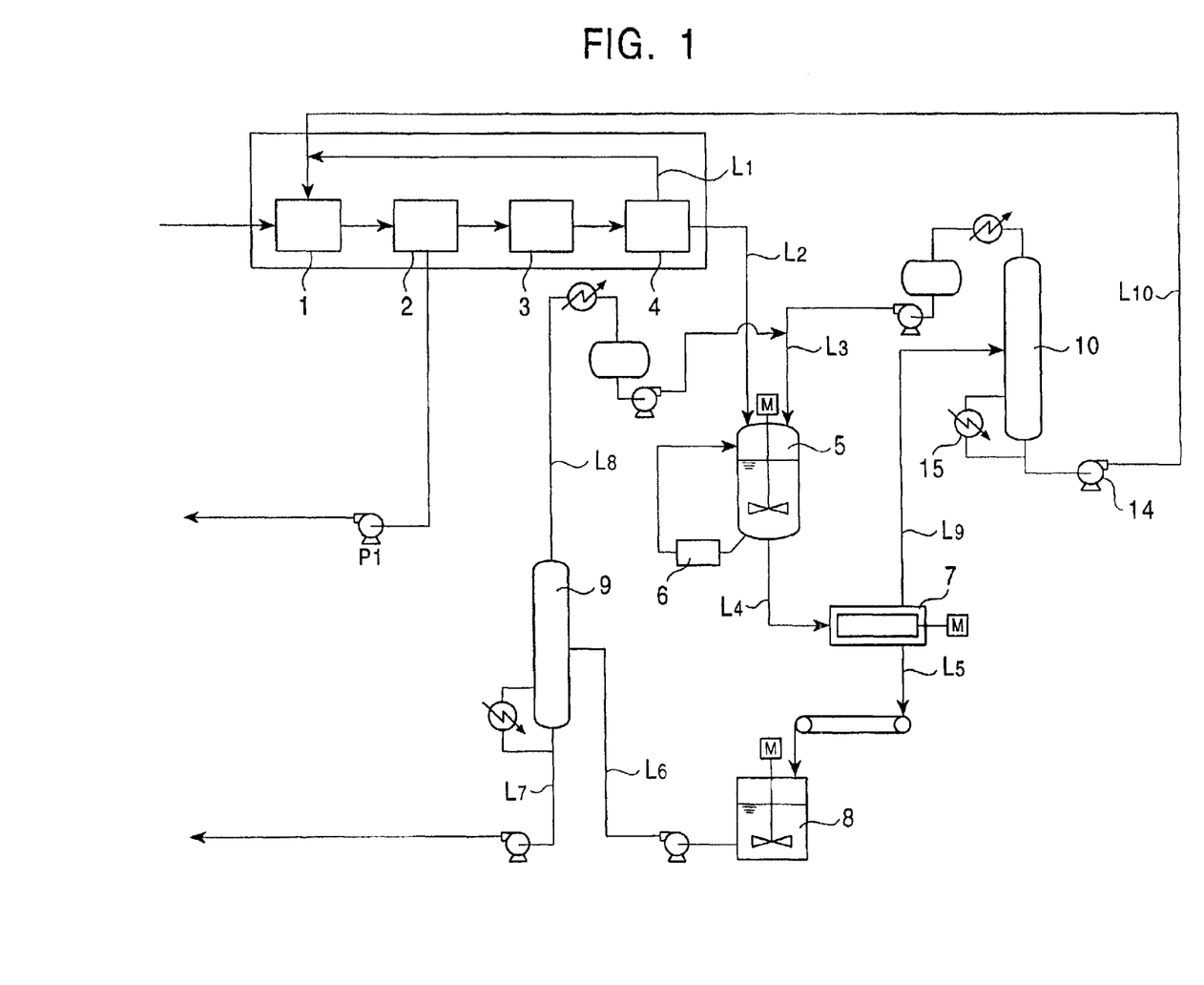
FIG. 1 is a schematic diagram showing a typical example of a method of the present invention.

FIG. 1 is a schematic view of a typical example of the present invention in which a two-stage process of cooling crystallization and press filtration is shown.

After a mixture containing DMN isomers used as a feedstock is fed into a first cooling crystallization device 1 and is then cooled to a temperature below the melting point of 2,6-DMN, the mixture is supplied to a first press filtration device 2. A slurry containing a crystal obtained by the cooling is separated into a solution (mother liquor) and a solid component (crystal) by solid-liquid separation in this device, and the mother liquor is supplied outside the production line or is supplied to a former step by a pump P1. At the same time, the crystal is supplied to a second cooling crystallization device 3 and is then crystallized by cooling as in the first stage, and subsequently, solid-liquid separation was performed in a second press filtration device 4. The mother liquor obtained in this step is returned to the first cooling crystallization device 1 via a line $L_1$. In addition, a crystal obtained in this step is supplied to a washing bath 5 via a line $L_2$. The crystal is mixed with a solvent supplied into the washing bath 5 via a line $L_3$ and is washed by stirring. During washing by stirring, a slurry in the washing bath is supplied to a wet-type pulverizer 6 provided outside the washing bath, and a cake is pulverized and is then returned to the washing bath 5. After washing by stirring, the slurry is supplied to a subsequent solid-liquid separation step via a line $L_4$ (hereinafter, an example in which a centrifuge is used in a solid-liquid separation step is shown; however, another solid-liquid separation method may also be used). A 2,6-DMN cake, which is obtained by solid-liquid separation using a centrifuge 7, is supplied to a melting bath 8 via a line $L_5$, and after melting, the molten cake is supplied to a distillation tower 9 via a line $L_6$. The molten cake is separated into a solvent component and a product, i.e., a highly pure 2,6-DMN, in the distillation tower 9. The highly pure 2,6-DMN thus obtained is recovered as a product via a line $L_7$. At the same time, the solvent is returned to the washing bath 5 via a line $L_8$ and the line $L_3$.

In addition, the solvent separated in the centrifuge 7 is supplied to a distillation tower 10 via a line $L_9$ and is then separated into a solvent component and a component of DMN mixture. The solvent component mentioned above is returned to the washing bath 5 via the line $L_3$, and the component of DMN mixture is returned to the first cooling crystallization device 1 via a line $L_{10}$.

FIG. 3 is a schematic view showing an example of a method for manufacturing 2,6-DMN in which washing treatment is performed at least twice, and as described above, the number of washing treatment may be increased or decreased in accordance with an object. A crystal (a solid component) obtained by solid-liquid separation using press filtration in a manner as described above is supplied to a washing bath 5A via a line $L_2$. The crystal described above is mixed with a solvent supplied into the washing bath 5A via a line $L_3$ and is washed by stirring. During washing by stirring, a slurry in the washing bath is supplied to a wet-type pulverizer 6 provided outside and is then returned to the washing bath 5A after a cake is pulverized. After washing by stirring, the slurry is supplied to a subsequent solid-liquid separation step (centrifuge 7) via a line $L_4$. A 2,6-DMN cake obtained by the solid-liquid separation using a centrifuge 7A is supplied to a washing bath 5B, which is a second washing bath, via a line $L_6$.

In addition, a mother liquor obtained by separation using the centrifuge 7A is supplied to a distillation tower 9 via a line $L_5$ and is then separated into a solvent component and a low purity 2,6-DMN. The solvent component separated by the distillation tower 9 is supplied to the washing bath 5B, which is the second washing bath, from a line $L_8$ via a line $L_{11}$. Washing by stirring is performed in the washing bath 5B, as in the washing bath 5A, for the cake mixed with the solvent which is supplied via the line $L_{11}$. After washing by stirring, a slurry is supplied to a solid-liquid separation step. In this solid-liquid separation step, an example using a centrifuge is described; however, another solid-liquid separation method may also be used. A 2,6-DMN cake obtained by solid-liquid separation using a centrifuge 7B is supplied to a melting bath 8 via a line $L_9$, and after melting, the molten cake is supplied to a distillation tower 9B via a line $L_{10}$, so that the molten cake is separated into a solvent component and a highly pure 2,6-DMN. The solvent component described above is returned to the washing bath 5B via the line $L_{11}$.

The solvent obtained by separation using the centrifuge 7B is returned to the washing bath 5A via a line $L_{12}$. In addition, a highly pure 2,6-DMN is recovered as a product from the distillation tower 9B via a line $L_{13}$.

Hereinafter, the present invention will be described in detail with reference to examples. However, the present invention is not limited to the examples described below, and it is understood that every modification made in accordance with the description in this specification is within the scope of the present invention. In the examples and comparative examples described below, "%" means "wt %".

EXAMPLE 1

A feedstock (mixture containing DMN isomers) having the composition shown in Table 1 was crystallized at 9° C. and was then processed by press filtration at approximately 100 kg/cm$^2$, thereby obtaining a cake of the mixture containing DMN isomers having the composition shown in Table 1. Next, 100 g of this crystal of the mixture containing DMN isomers and 200 g of normal hexane were placed in a separable flask provided with a stirrer and were then stirred at 30° C. for 1 hour. Subsequently, after a crystal was separated by suction filtration, 100 g of a pure solvent was poured over the crystal. When the crystal was analyzed using gas chromatography, it was found that a crystal having the composition shown in Table 1 was obtained. As "other impurities", there were methylnaphthalene, ethylnaphthalene, hydrocarbons having boiling points equivalent to those of the other DMN's, and the like.

TABLE 1

| Composition (wt %) | Feedstock | Cake after Cooling crystallization/ Press Filtration | Filtrate after Cooling crystallization/ Press Filtration | Crystal after Washing (Example 1) |
|---|---|---|---|---|
| 2,6-DMN | 11.68 | 75.72 | 9.30 | 97.66 |
| 2,7-DMN | 12.03 | 10.54 | 12.09 | 2.34 |
| Other DMN isomers | 26.23 | 6.01 | 6.01 | Below detection limit |
| Other Impurities | 50.06 | 7.93 | 7.93 | Below detection limit |
| Total | 100.00 | 100.00 | 100.00 | 100.00 |

The yield with respect to 2,6-DMN in the cake before washing was 65.71%. It was understood that 2,6-DMN could be obtained with a high yield according to the present invention.

EXAMPLE 2

A cake of a mixture containing DMN isomers having the composition shown in Table 2 and a crystal formed therefrom after washing were obtained in a manner equivalent to that in example 1 except that a feedstock (mixture containing DMN isomers) having the composition shown in Table 2 was crystallized at 15° C. in a first stage and was then crystallized at 70° C. in a second stage, and that press filtration was performed at approximately 100 kg/cm$^2$ after each cooling crystallization mentioned above.

TABLE 2

| Composition (wt %) | Feedstock | Cake after First Cooling Crystallization | Filtrate after First Cooling Crystallization | Cake after Second Cooling Crystallization | Filtrate after Second Cooling Crystallization | Crystal after Washing (Example 2) |
|---|---|---|---|---|---|---|
| 2,6-DMN | 11.68 | 58.00 | 11.21 | 80.04 | 52.61 | 99.16 |
| 2,7-DMN | 12.03 | 6.00 | 12.09 | 4.92 | 6.28 | 0.80 |
| Other DMN isomers | 26.23 | 15.00 | 26.34 | 13.36 | 15.44 | Below Detection Limit |
| Other Impurities | 50.06 | 21.00 | 50.35 | 2.58 | 25.66 | 0.04 |
| Total | 100.00 | 100.00 | 100.00 | 100.00 | 100.00 | 100.00 |

The yield with respect to 2,6-DMN in the cake before washing was 65.05%. It was understood that 2,6-DMN could be obtained with a high yield according to the present invention.

EXAMPLE 3

A cake of a mixture containing DMN isomers having the composition shown in Table 3 and a crystal formed therefrom after washing were obtained in a manner equivalent to that in example 1 except that a feedstock (mixture containing DMN isomers) having the composition shown in Table 3 was crystallized at 3° C. and was then processed by solid-liquid separation using a centrifuge in a first stage, and in a second stage, a crystal was precipitated at 65.8° C. and was then processed by press filtration using a tube press at an operation pressure of 100 kg/cm$^2$. As the tube press in this example, TPS-1 provided with temperature control function manufactured by Ashizawa Co., Ltd. was used in which the filtration area was 0.45 m$^2$ and the inside volume was 17 liter.

TABLE 3

| Composition (wt %) | Feedstock | Cake after First Cooling Crystallization | Filtrate after First Cooling Crystallization | Cake after Second Cooling Crystallization | Filtrate after Second Cooling Crystallization | Crystal after Washing (Example 3) |
|---|---|---|---|---|---|---|
| 2,6-DMN | 10.98 | 41.1 | 8.0 | 95.56 | 35.73 | 100.00 |
| 2,7-DMN | 12.56 | 14.7 | 12.1 | 2.73 | 16.73 | Below Detection Limit |
| Other Impurities | 76.50 | 44.3 | 79.9 | 1.71 | 47.50 | Below Detection Limit |
| Total | 100.00 | 100.00 | 100.00 | 100.00 | 100.00 | 100.00 |

The yield with respect to 2,6-DMN in the cake before washing was 77.24%. It was understood that 2,6-DMN could be obtained with a high yield according to the present invention.

EXAMPLE 4

A cake of a mixture containing DMN isomers having the composition shown in Table 4 and a crystal formed therefrom after washing were obtained in a manner equivalent to that in example 1 except that a feedstock (mixture containing DMN isomers) having the composition shown in Table 4 was crystallized at 29° C. and was then processed by press filtration at approximately 100 kg/cm$^2$.

TABLE 4

| Composition (wt %) | Feedstock | Cake after Cooling crystallization/ Press Filtration | Filtrate after Cooling crystallization/ Press Filtration | Crystal after Washing (Example 4) |
|---|---|---|---|---|
| 2,6-DMN | 20.46 | 83.93 | 14.19 | 99.10 |
| 2,7-DMN | 10.53 | 4.74 | 11.72 | 0.78 |
| Other DMN isomers | 22.45 | 4.32 | 25.49 | 0.12 |
| Other Impurities | 46.56 | 7.01 | 48.60 | Below detection list |
| Total | 100.00 | 100.00 | 100.00 | 100.00 |

The yield with respect to 2,6-DMN in the cake before washing was 66.66%. It was understood that 2,6-DMN could be obtained with a high yield according to the present invention.

EXAMPLE 5

Multistage washing including return of a mother liquor was performed as described below.

(1) A feedstock (mixture containing DMN isomers) having the composition shown in Table 5 was crystallized at 32° C. and was then processed by press filtration at approximately 100 kg/cm$^2$, thereby obtaining a cake of the mixture containing DMN isomers having the composition shown in Table 5.

(2) Next, 545 g of this crystal of the mixture containing DMN isomers and 660 g of normal hexane were placed in a separable flask provided with a stirrer and were then stirred at 30° C. for 1 hour. Subsequently, the crystal was separated by press filtration, and the mother liquor was recovered.

(3) Next, by using 165 g of the crystal of the mixture containing DMN isomers obtained in the above (1) and 660 g of the mother liquor obtained in the above (2), washing treatment was performed in a manner equivalent to that performed in the above (2) except that the temperature was set to 35° C. Subsequently, the crystal was separated by centrifugation.

(4) In addition, by using 128 g of the crystal obtained in the above (3) and 411 g of normal hexane, washing treatment was performed in a manner equivalent to that performed in the above (2). Subsequently, the crystal was separated by press filtration, and when the crystal thus obtained was analyzed using gas chromatography, it was found that the crystal had the composition shown in Table 5. The yield with respect to 2,6-DMN in the cake before washing was 45%.

TABLE 5

| Composition (wt %) | Feedstock | Cake after Cooling Crystallization | Filtrate after Cooling Crystallization | Crystal after First Washing ((2) in This Example) | Crystal after Second Washing ((4) in This Example) |
|---|---|---|---|---|---|
| 2,6-DMN | 21.84 | 81.77 | 15.39 | 97.76 | 99.05 |
| 2,7-DMN | 18.76 | 7.76 | 18.49 | 1.98 | 0.87 |
| Other DMN isomers | 57.46 | 9.93 | 61.18 | 0.26 | 0.08 |
| Other Impurities | 4.43 | 0.54 | 4.94 | Below Detection Limit | Below Detection Limit |
| Total | 100.00 | 100.00 | 100.00 | 100.00 | 100.00 |

Comparative Example 1

A cake of the mixture containing DMN isomers having the composition shown in Table 6 and a crystal formed therefrom after washing were obtained in a manner equivalent to that in example 1 except that the a feedstock (mixture containing DMN isomers) having the composition shown in Table 6 was crystallized at 26° C. and was then processed by suction filtration while approximately 2 kg/cm² was applied.

TABLE 6

| Composition (wt %) | Feedstock | Cake after Cooling crystallization/ Suction Filtration | Filtrate after Cooling crystallization/ Suction Filtration |
|---|---|---|---|
| 2,6-DMN | 21.95 | 37.74 | 15.09 |
| 2,7-DMN | 10.45 | 7.50 | 11.24 |
| Other Impurities | 67.50 | 54.76 | 73.67 |
| Total | 100.00 | 100.00 | 100.00 |

The purity of 2,6-DMN in the crystal obtained after washing was less than 70%.

INDUSTRIAL APPLICABILITY

As has thus been described, according to the method of the present invention, even when a DMN mixture containing 5 wt % or more of 2,7-DMN is used as a feedstock, a highly pure 2,6-DMN can be manufactured, and in addition, even when a DMN mixture containing less than 25 wt % of 2,6-DMN is processed by cooling crystallization, a highly pure 2,6-DMN can be manufactured. In particular, when a solid component containing 80% or more of 2,6-DMN is washed using a solvent and was then processed by solid-liquid separation and distillation, a 2,6-DMN having a high purity of 99% or more can be obtained.

What is claimed is:

1. A method for making 2,6-dimethylnaphthalene comprising:
   performing cooling crystallization of a mixture containing dimethylnaphthalenes which includes 2,6-dimethylnaphthalene;
   performing solid-liquid separation which includes press filtration to obtain a solid component; and
   washing the solid component using a solvent which is an aliphatic and/or alicyclic hydrocarbon;
   wherein washing is performed at least twice, and a part or the entirety of a mother liquor obtained in the second washing or in a subsequent washing is used as a solvent in a washing performed prior to the washing at which the mother liquor is obtained.

2. The method according to claim 1,
   wherein the mixture containing dimethylnaphthalenes is a mixture composed of dimethylnaphthalene isomers.

3. The method according to claim 1,
   wherein the solid-liquid separation includes press filtration performed at a pressure of 10 kg/cm² or more.

4. The method according to claim 1,
   wherein the mixture containing dimethylnaphthalenes is used as a feedstock and includes 5 wt % or more of 2,7-dimethylnaphthalene.

5. The method according to claim 1, wherein the cooling crystallization is performed for a mixture containing dimethylnaphthalenes which includes less than 25 wt % of 2,6-dimethylnaphthalene.

6. The method according to claim 1, wherein washing is performed for a solid component containing 80% or more of 2,6-dimethylnaphthalene using an aliphatic and/or alicyclic hydrocarbon solvent, and
   further comprising performing solid-liquid separation and distillation after the washing step, whereby a 2,6-dimethylnaphthalene having a purity of 99% or more is obtained.

7. The method according to claim 1,
   wherein the solvent used in for washing is an aliphatic hydrocarbon and/or alicyclic hydrocarbon having 5 to 10 carbon atoms.

8. The method according to claim 1,
   wherein the press filtration is performed using a tube press.

9. The method of claim 1, which comprises washing the solid component in an aliphatic hydrocarbon.

10. The method of claim 1, which comprises washing the solid component in an alicyclic hydrocarbon.

11. The method of claim 1, which comprises washing the solid component in hexane.

12. The method of claim 1, which comprises washing the solid component in octane.

13. The method of claim 1, wherein the 2,6-dimethylnaphthalene obtained has a purity of 99% or more.

* * * * *

UNITED STATES PATENT AND TRADEMARK OFFICE
CERTIFICATE OF CORRECTION

PATENT NO. : 6,894,202 B1
DATED : May 17, 2005
INVENTOR(S) : Yamamoto et al.

It is certified that error appears in the above-identified patent and that said Letters Patent is hereby corrected as shown below:

<u>Title page,</u>
Item [45], should read
-- [45] **Date of Patent: \*May 17, 2005**
  [\*] Notice: Subject to any disclaimer, the term of this
      patent is extended or adjusted under 35
      U.S.C. 154(b) by 48 days.

This patent is subject to a terminal disclaimer. --

Item [73], should read as follows:
 -- [73] Assignee: **Kabushiki Kaisha Kobe Seiko Sho
          (Kobe Steel, Ltd.)**, Kobe (JP) --

Signed and Sealed this

Nineteenth Day of July, 2005

JON W. DUDAS
*Director of the United States Patent and Trademark Office*